USOO5563339A

United States Patent [19]
Compton et al.

[11] Patent Number: 5,563,339
[45] Date of Patent: Oct. 8, 1996

[54] SELF-CORRECTING AUTOCALIBRATING VAPOR PRESSURE ANALYZER

[75] Inventors: Jack R. Compton; Joe L. De La Cruz; Gregory S. Schmid, all of San Antonio, Tex.

[73] Assignee: Southwest Research Institute, San Antonio, Tex.

[21] Appl. No.: 393,982

[22] Filed: Feb. 24, 1995

[51] Int. Cl.[6] .................................................. G01N 7/00
[52] U.S. Cl. ........................................ 73/64.45; 73/29.01
[58] Field of Search .............................. 73/29.01, 29.03, 73/29.05, 64.45

[56] References Cited

U.S. PATENT DOCUMENTS

| | | | |
|---|---|---|---|
| 3,499,317 | 3/1970 | Hook. | |
| 4,332,159 | 6/1982 | Chin et al. | 73/64.2 |
| 4,395,903 | 8/1983 | Gouw | 73/64.2 |
| 4,491,016 | 1/1985 | Haefner | 73/302 |
| 4,522,056 | 6/1985 | Chin et al. | 73/64.2 |
| 4,783,989 | 11/1988 | Reed | 73/64.2 |
| 4,900,405 | 2/1990 | Otagawa et al. | 204/1 T |
| 4,990,058 | 2/1991 | Eslinger | 417/46 |
| 5,164,053 | 11/1992 | Razaq et al. | 204/153.18 |
| 5,172,586 | 12/1992 | Reed | 73/64.45 |
| 5,191,786 | 3/1993 | Baughman et al. | 73/64.45 |

OTHER PUBLICATIONS

ASTM Designation: D 5190–93a "Standard Test Method for Vapor Pressure of Petroleum Products (Automatic Method)[1]", standard, Aug., 1993, pp. 394–398.

ASTM Designation: D 5191–93a "Standard Test Method for Vapor Pressure of Petroleum Products (Mini Method)[1]", standard, Aug., 1993, pp. 399–402.

ASTM Designation: D 5191–91 "Standard Test Method of Vapor Pressure of Petroleum Products (Mini Method)[1]", standard, Jan., 1992, pp. 404–407.

ASTM Designation: D 5188–93 "Standard Test Method for Vapor–Liquid Ratio Temperature Determination of Fuels (Evacuted Chamber Method)", standard, Oct., 1993, pp. 389–392.

Precision Scientific Petroleum Instruments Co., "Reid Monitor Catalog 44800D/44800E", bulletin, undated.

Precision Scientific Petroleum Instruments Co., "In the Lab", newsletter, Spring/Summer 1994.

Grabner Instruments, "CCA VP Automatic Vapor Pressure Tester", brochure and product bulletin, distributed and stocked by Petrolab Corporation, undated.

Grabner Instruments, "CCA VPS Fully Automatic Portable Vapor Pressure Tester", brochure and product bulletin, distributed and stocked by Petrolab Corporation, undated.

ASTM Designation: D 5189–91 "Standard Test Method for Temperature Corresponding to Vapor–Liquid Ratio of 20 for Gasoline and Gasoline–Oxygenate Blends (Bomb Method)[1]", standard, Dec., 1991, pp. 393–398.

Walter Herzog GmbH, "Herzog Automatic Petroleum Analyzers", brochure, undated.

Walter Herzog GmbH, "Herzog's Petroleum Vapor Pressure Analyzers", brochure, undated.

(List continued on next page.)

*Primary Examiner*—Hezron E. Williams
*Assistant Examiner*—Jay L. Politzer
*Attorney, Agent, or Firm*—Akin, Gump, Strauss, Hauer & Feld, L.L.P.

[57] ABSTRACT

A self-correcting autocalibrating analyzer for the direct determination of liquid vapor pressure and determination of the temperature at which a given ratio of vapor to liquid will exert a predetermined pressure in a container of predetermined volume. Test volumes within the analyzer can be automatically calibrated, and corrections for dissolved air in the liquid sample and/or for temperature-related changes in the liquid sample size can be made. The analyzer can set an alarm when unprogrammed variation is detected in preset volumes or when successive vapor pressure determinations of standard liquids vary by more than a predetermined amount.

11 Claims, 2 Drawing Sheets

OTHER PUBLICATIONS

ABB, "Vista Model 4100 On–Line RVP Analyzer", brochure, 1992.

ABB, by Stephen M. Bostic and James M. Floyd, "A New On–Line Reid Vapor Pressure Instrument Concept", SC7–3–1290, booklet, undated.

ABB, by Stephen M. Bostic and James M. Floyd, "On–Line RVP Analysis for Gasoline Blending", SC7–5–691, booklet, undated.

ABB, "LPG/NGL Process Analyzer Model 4102", brochure, undated.

ABB, by Stephen M. Bostic, "A New On–Line LPG Vapor Pressure Analyzer", SC7–16–294, booklet, undated.

Grabner Instruments, "Mini Flash Fully Automatic Flash Point Tester", brochure and price list, distributed and stocked by Petrolab Corporation, undated.

SRI, Donald L. Lazzari, Manager, Department of Petroleum Products and Emissions Research Division, "Automatic Vapor Pressure Instrument", brochure, undated.

Southwest Research Institute, Petroleum Product Research Department 'Capabilities' brochure entitled "Automatic On–Line Reid Vapor Pressure—Vapor/Liquid Ratio Measurement Appliance" dated Feb. 1995.

SELF-CORRECTING AUTOCALIBRATING VAPOR PRESSURE ANALYZER

FIELD OF THE INVENTION

The invention relates to methods and apparatus for vapor pressure and vapor-liquid ratio measurements on liquids. Also included are methods and apparatus for analyzer autocalibration and for calculation of corrected vapor pressure and vapor-liquid ratio values based on liquid sample parameters.

BACKGROUND

Vapor pressure measurements for hydrocarbons

Vapor pressure is the pressure exerted when a solid or liquid is in equilibrium with its own vapor. Stated another way, vapor pressure is a measure of the tendency of a substance to vaporize. Thus, vapor pressure values are useful in determinations of a liquid fuel's volatility, vapor locking tendency, engine performance, and potential for evaporation loss. Of these characteristics, the tendency of a liquid fuel to evaporate has particular relevance for refiners and fuel blenders. Fuel vapor is an important contributor to air pollution in certain areas, and the Environmental Protection Agency (EPA) has begun to enforce regulations to limit evaporative fuel losses. Violation of EPA-imposed vapor pressure limits on liquid fuels can lead to significant economic losses due to fines and product recalls.

Specifically, in June 1989 the vapor pressure of gasoline blended for summertime use was limited to 10.5 pounds per square inch (psi) in most states and 9.0 psi in certain areas. The applicability of these limits has since been broadened, and analogous limits have been set for other petroleum products such as diesel and jet fuels. To test their liquid fuel products for compliance with the limits, petroleum refiners and blenders use analyzers capable of direct individual sample or on-line determination of Reid Vapor Pressure (RVP). Because many fuels, including gasolines, diesel fuels, and jet fuels, are blends of hydrocarbons having different boiling points, the aggregate RVP of liquid mixtures must be determined.

To ensure the accuracy of such vapor pressure values, corrections to the RVP may be made to compensate for the partial pressure of dissolved air which may be present in the samples tested. It is also particularly important in testing fuel mixtures that certain measured volumes of the test apparatus be very accurately determined. This requirement is somewhat less stringent when dealing with a pure substance because the main factors determining a pure liquid's vapor pressure are the chemical composition of the liquid and its temperature. The relative amounts of a pure liquid and its vapor do not affect the equilibrium vapor pressure determination as long as some liquid is present. In contrast, the total vapor pressure of liquid mixtures with differing component vapor pressures depends on such factors as the ratio of vapor space to liquid volume in the liquid's container, as well as the temperature, chemical composition, and the amount of dissolved air in the liquid mixture. Hence, total vapor pressure determinations for fuel mixtures is a relatively exacting process.

The original method for determining the vapor pressure of liquid hydrocarbon fuels (either pure or mixtures) is reflected in the test for RVP defined by the American Society for Testing and Materials (ASTM) standard D4953. This method reduces variations in vapor pressure determinations by requiting uniform saturation of each test sample with dissolved air at a temperature between 32 and 40 degrees Fahrenheit. While this saturation step is beneficial when properly performed, error is introduced if the specified test volume of the saturated test sample is not actually drawn at a temperature within the allowed range.

For example, if a fluid test example is allowed to warm to a temperature above 40 degrees Fahrenheit (not an uncommon occurrence), the sample will expand and the fluid density will be reduced. A specified volume drawn from the warmed fluid will then contain less fluid mass than the same specified volume would contain if drawn from a test sample at a lower temperature. Variations in the mass of fluid introduced into a vapor pressure test instrument will cause errors in the vapor pressure determinations, and there is currently no procedure for correction of this error in the ASTM standard. Currently avail, able commercial instruments for vapor pressure measurements do not make such a correction. Hence, for fuel samples believed to have a RVP below 26 psi (i.e., most gasolines, diesels and jet fuels), following the ASTM method would ideally mean holding the fluid sample very close to the (chilled) temperature at which air saturation is carried out until the specified volume is drawn for injection into the test instrument.

The instrument for performing the ASTM RVP test includes a "gasoline" chamber and an "air" chamber, with the volume ratio of the air chamber to the gasoline chamber between the limits of 3.8 and 4.2 to 1. After preforming the chilling and air saturation steps, a fuel test sample is injected into the gasoline chamber. The air chamber (preheated to 100 degrees Fahrenheit) is then attached to the gasoline chamber so that there is an open path between the two chambers for fuel sample liquid and vapors (the test chamber expansion step). The combined chambers are immersed in a constant temperature bath at 100° F. and periodically shaken until thermal equilibrium is achieved. The total pressure of the vapor and air above the remaining liquid sample is measured and reported as the RVP.

The Reid Method as specified in ASTM D4953, though extremely useful, involves tedious and time-consuming manual operations. Because of the need for obtaining accurate, precise, and reproducible results, the careful attention of one skilled in performing the test is required for 30 minutes or more per RVP determination. Because current regulations mandate frequent RVP measurements, it would be highly desirable: to shorten the test time for each one while maintaining (or improving) the accuracy, precision, and reproducibility of the original test method in an automatic on-line instrument.

Two additional ASTM test procedures are available to help meet these requirements, i.e., ASTM D5190 and ASTM D5191. These procedures allow rapid and precise determinations of vapor pressures that correlate well with the RVP data obtained by one skilled in conducting the ASTM D4953 test. Instruments developed to use these procedures, however, are generally capable of either laboratory or on-line use but not both. They also do not provide for a measurement indicative of the vapor-liquid ratio, which is often used in conjunction with RVP to characterize fuels.

The result of a vapor-liquid ratio test is actually the temperature at which a predetermined test volume of fluid will exert a predetermined pressure within a closed container having a predetermined volume. This ratio test temperature can then be related to the tendency of a fuel to vaporize in automobile fuel systems (causing vapor-lock). The most commonly used method for determining the vapor-liquid ratio of spark-ignition engine fuels is that of ASTM D2533-

90. Unfortunately, this procedure is a lengthy wet-chemical laboratory method which requires mercury as a containing liquid, which makes the procedure hazardous. In addition, errors related to improper control of sample air saturation and temperature may occur just as in the RVP test. It is apparent, then, that the above RVP and ratio test temperature determinations are both subject to significant errors, even when they are performed according to published guidelines. This may be due in part to the historical evolution of these tests, which originally were performed using equipment which made calibration and error correction relatively difficult.

SUMMARY OF THE INVENTION

The self-correcting autocalibrating analyzer of the present invention, on the other hand, has been designed to facilitate autocalibration of test chamber volumes (by reference to at least one prior test chamber volume calibration), and vapor pressure values and ratio test temperatures (by reference to at least one known standard). Self-correction is provided for errors which are a function of test sample temperature and air saturation. In laboratory tests, such analyzers have been found to give rapid and precise determinations of vapor pressures that correlate well with RVP's obtained through skilled conduct of the ASTM D4953 test, as well as the ASTM D5190 and D5191 automatic vapor pressure procedures. Rapid and precise determinations of ratio test temperatures characteristic of a fluid's vapor-liquid ratio at a predetermined pressure and volume are also possible with the analyzer. Such ratio test temperatures correlate well with data obtained using the ASTM D2533-90 vapor-liquid ratio test procedure.

Further, use of the analyzer for a single RVP determination requires less than one minute of operator time and provides the required vapor pressure data within about four minutes of test start. Determination of a ratio test temperature with the analyzer takes about ten to twelve minutes. During automatic on-line operation, virtually no operator time is required, and the instrument can automatically switch between RVP and ratio test temperature determinations.

Although it measures vapor pressure, the self-correcting analyzer indicates RVP. By computer analysis of a large number of hydrocarbons, a nearly linear relationship has been found between the absolute vapor pressure measured by the analyzer and RVP as measured by ASTM D4953. This is especially true in the range of ordinary gasoline RVP values of 5 psi and 15 psi. Because the relationship is not quite linear, the instrument is not used for providing direct RVP data outside of the calibration range. However, it is sometimes desirable to measure the RVP of samples having a pressure slightly above or below the calibration range, e.g. 2 to 5 psi or 16 to 20 psi. Although the instrument will not give a direct reading of RVP in these ranges, correction factors are applied to the indicated instrument reading to arrive at the RVP. The correction factors can be derived either from the above mentioned computer correlation or from separate determinations of RVP of standard samples using both the instrument and ASTM D4953.

A preferred embodiment of the vapor pressure analyzer of the present invention comprises a hollow cylinder of substantially right circular cylindrical shape, the cylinder having a wall, first and second ends, and a longitudinal axis passing through and substantially parallel to the first and second ends. Cylinder temperature control means are included for attaining a desired temperature within the cylinder, and a piston is positionable slidingly and sealingly within the hollow cylinder. A piston rod is coupled to the piston and passes slidingly and sealingly through a hole in the first cylinder end to control longitudinal movement of the piston within the cylinder. An adjustable piston rod driver is coupled to the piston rod for adjusting piston longitudinal position within the cylinder and for producing a signal indicative of the piston longitudinal position within the cylinder.

Calibration means for calibrating the adjustable piston rod driver by reference to at least one prior adjustable piston rod calibration are provided. First and second piston position sensors within the cylinder wall proximate the first and second cylinder ends respectively produce first and second piston position sensor signals indicative of first and second longitudinal piston positions within the cylinder.

There is an inlet port and an outlet port in the cylinder first end, and a fluid inlet pipe and a fluid outlet pipe are coupled sealingly to the inlet and outlet ports respectively. At least one inlet valve and an outlet valve are in line with the fluid inlet and outlet pipes respectively, and there is at least one pressure sensor for producing a signal indicative of pressure within the cylinder. There is also at least one temperature sensor for producing a signal indicative of cylinder temperature, and at least one temperature sensor for producing a signal indicative of fluid temperature of fluid within said fluid inlet pipe.

An analyzer controller produces control signals for the cylinder temperature control means, the adjustable piston rod driver, and the inlet and outlet valves as functions of first and second piston position sensor signals, a cylinder pressure signal, at least one cylinder temperature signal, and at least one fluid inlet fluid temperature signal.

The analyzer controller comprises calculator means for calculating a volume correction as a function of the fluid temperature of fluid within the fluid inlet pipe, for calculating a vapor pressure value for a liquid within the cylinder, for calibrating the vapor pressure value against a standard, for calculating a ratio test temperature for a liquid within the cylinder, and for calibrating the ratio test temperature against a standard. Display means are included for displaying at least the vapor pressure and the ratio test temperature for the liquid within the cylinder.

The above vapor pressure analyzer may additionally comprise an air saturation sensor for producing a signal indicative of air saturation of a fluid within the fluid inlet pipe. In this configuration, calculator means for calculating a vapor pressure correction value and a ratio test temperature correction as a function of the air saturation of fluid within the fluid inlet pipe are included. Additional features of the invention are found in the detailed description below.

DETAILED DESCRIPTION

Analyzer structure and function

Figure 1:
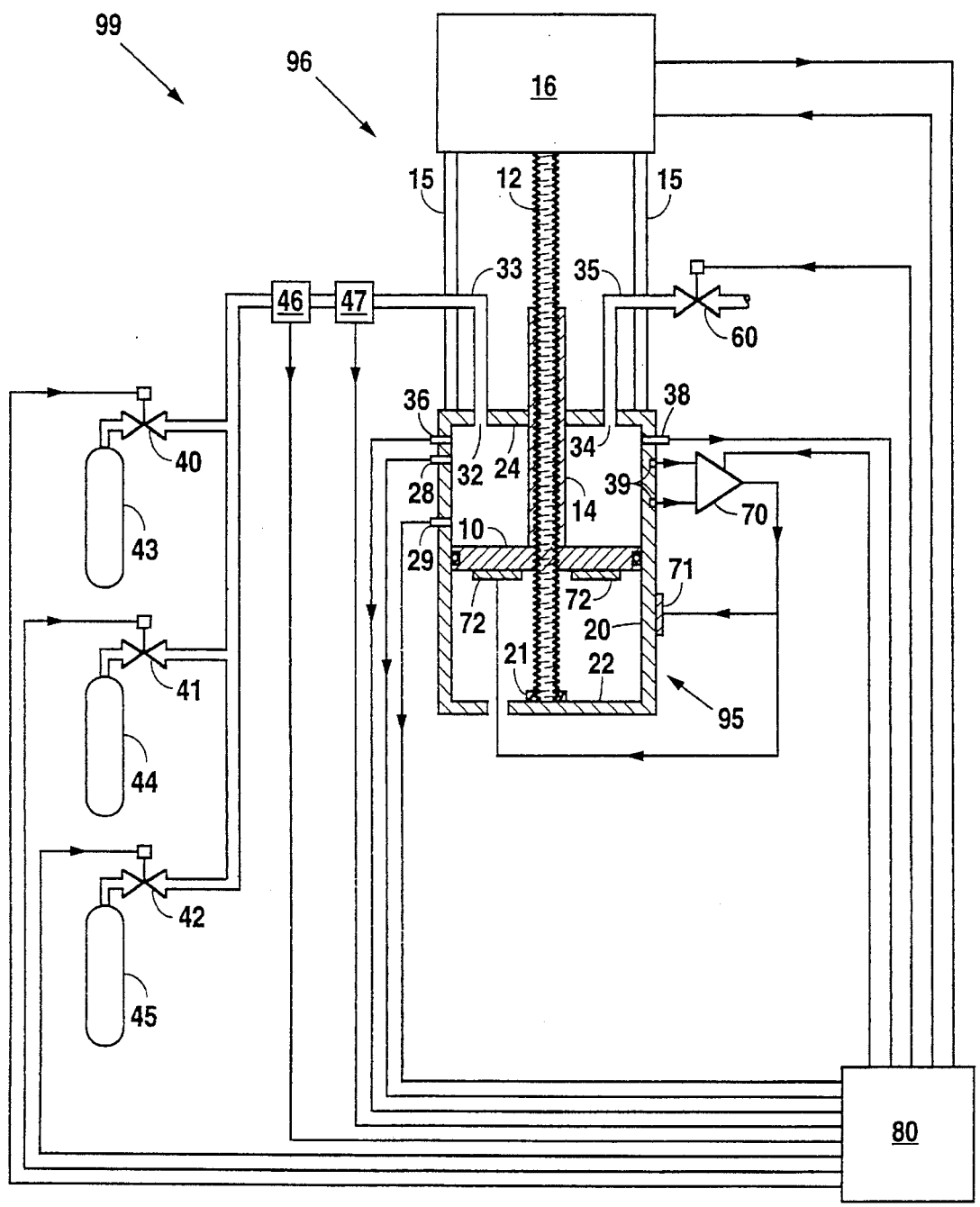
FIG. 1 schematically illustrates a self-correcting autocalibrating vapor pressure analyzer.

FIG. 1 schematically illustrates a self-correcting autocalibrating vapor pressure analyzer, comprising a hollow cylinder 95 of substantially right circular cylindrical shape. The cylinder 95 has a wall 20, first and second ends 24,22 respectively, and a longitudinal axis passing through and substantially perpendicular to the first and second ends 24,22. Cylinder temperature control means for attaining a desired temperature within cylinder 95 comprise, in the embodiment illustrated in FIG. 1, Peltier effect elements 71,72 which are thermally coupled to the cylinder wall 20 and piston 10 respectively. Cylinder temperature control means also comprises temperature controller 70 which controls both polarity and amplitude of electrical current supplied to Peltier effect elements 71,72 to achieve heating or cooling of cylinder 95 and piston 10. A cylinder temperature set point for temperature controller 70 is provided by analyzer controller 80, and cylinder temperature itself is provided to temperature controller 70 by at least one temperature sensor 39. Temperature sensors 39 (and other temperature sensors used herein) may comprise, for example, a thermistor or thermocouple, and temperature controller 70 may be a conventional proportional temperature controller well known to those skilled in the art. Note that analogous temperature control means may include in place of or in addition to the Peltier elements an oil or water bath surrounding at least a part of cylinder 95 and containing at least one heat exchanger for heating and cooling the bath as needed to control cylinder temperature.

A piston 10 is positionable slidingly and sealingly within hollow cylinder 95. A piston rod 14 is coupled to piston 10 and passes slidingly and sealingly through a hole in the first cylinder end 24 to control longitudinal movement of piston 10 within cylinder 95. An adjustable piston rod driver 96 is coupled to the piston rod 14 for adjusting the longitudinal position of piston 10 within cylinder 95 and for producing a signal for controller 80 indicative of piston longitudinal position within cylinder 95. Piston rod driver 96 comprises, in the embodiment illustrated in FIG. 1, a stepper motor 16 which is coupled to cylinder 95 through stand-offs 15 and which drives a lead screw 12. Lead screw 12 rests in bearing 21 which is attached to cylinder end 22 (as, for example, by screws). Threads on lead screw 12 engage mating threads internal to piston rod 14, and rotation of lead screw 12 thus results in longitudinal movement of piston rod 14 and piston 10 relative to cylinder 95.

Because stepper motor 16 rotates in relatively small angular increments and because lead screw 12 may have fine threads and is longitudinally fixed with respect to cylinder 95 by bearing 21, the longitudinal position of piston 10 may be adjusted precisely and repeatably. To provide a further check on longitudinal positioning of piston 10, optoelectronic sensors 28,29 are positioned in cylinder wall 20 proximate the normal limits of longitudinal travel of piston 10. Periodic calibration of the number of pulses required for stepper motor 16 to move piston 10 between positions detected by sensors 28,29 can confirm normal operation of piston rod driver 96 if the difference in the number of pulses required (pulse error value) for the present test compared to one or more past tests does not exceed a predetermined value (pulse error limit).

As applied to the illustrated embodiment of the invention, calibration means for calibrating the adjustable piston rod driver comprises a stored program comprising the following steps. First, one stores a standard value of stepper motor pulses needed to move piston 10 from a first position proximate the first piston position sensor 28 to a second position proximate the second piston position sensor 29. Then the adjustable piston rod driver 96 is commanded to move piston 10 to the first position proximate the first piston position sensor 28, after which driver 96 is commanded to move piston 10 to the second position proximate the second piston position sensor 29. One counts the pulses to stepper motor 16 required to move the piston 10 from the first position to the second position to form a new sum of stepper motor pulses. The standard value of stepper motor pulses is subtracted from the new sum of stepper motor pulses to form a pulse error value, and an alarm is set if the pulse error value exceeds a previously determined pulse error limit.

First and second piston position sensors 28,29 within cylinder wall 20 proximate first and second cylinder ends 24,22 respectively produce first and second piston position sensor signals indicative of first and second longitudinal piston positions within cylinder 95. These piston position sensors are preferably highly repeatable, with very small positional uncertainty. Optoelectronic sensors are acceptable but may be replaced with other sensor types having similar characteristics.

An inlet port 32 and an outlet port 34 in cylinder first end 24 allow liquids to be introduced to and removed from cylinder 95. A fluid inlet pipe 33 and a fluid outlet pipe 35 are both coupled sealingly to inlet and outlet ports 32,34 respectively. At least one inlet valve 40,41,42 and an outlet valve 60 are in line with the fluid inlet and outlet pipes 33,35 respectively. The valves may be manually controlled, but in preferred embodiments, they will be electrically controlled by analyzer controller 80.

Analyzer controller 80 preferably comprises an electronic computer having at least one program stored in memory 82, although all of its functions may be performed by a human operator with an instrument providing input and output signal conditioning as provided by conditioners 85,86 respectively. Memory 82 will preferably also be used to store at least a signal indicative of the longitudinal position of piston 10 within cylinder 95, and more preferably to store at least the vapor pressure and the ratio test temperature values for a liquid within cylinder 95.

Figure 2:
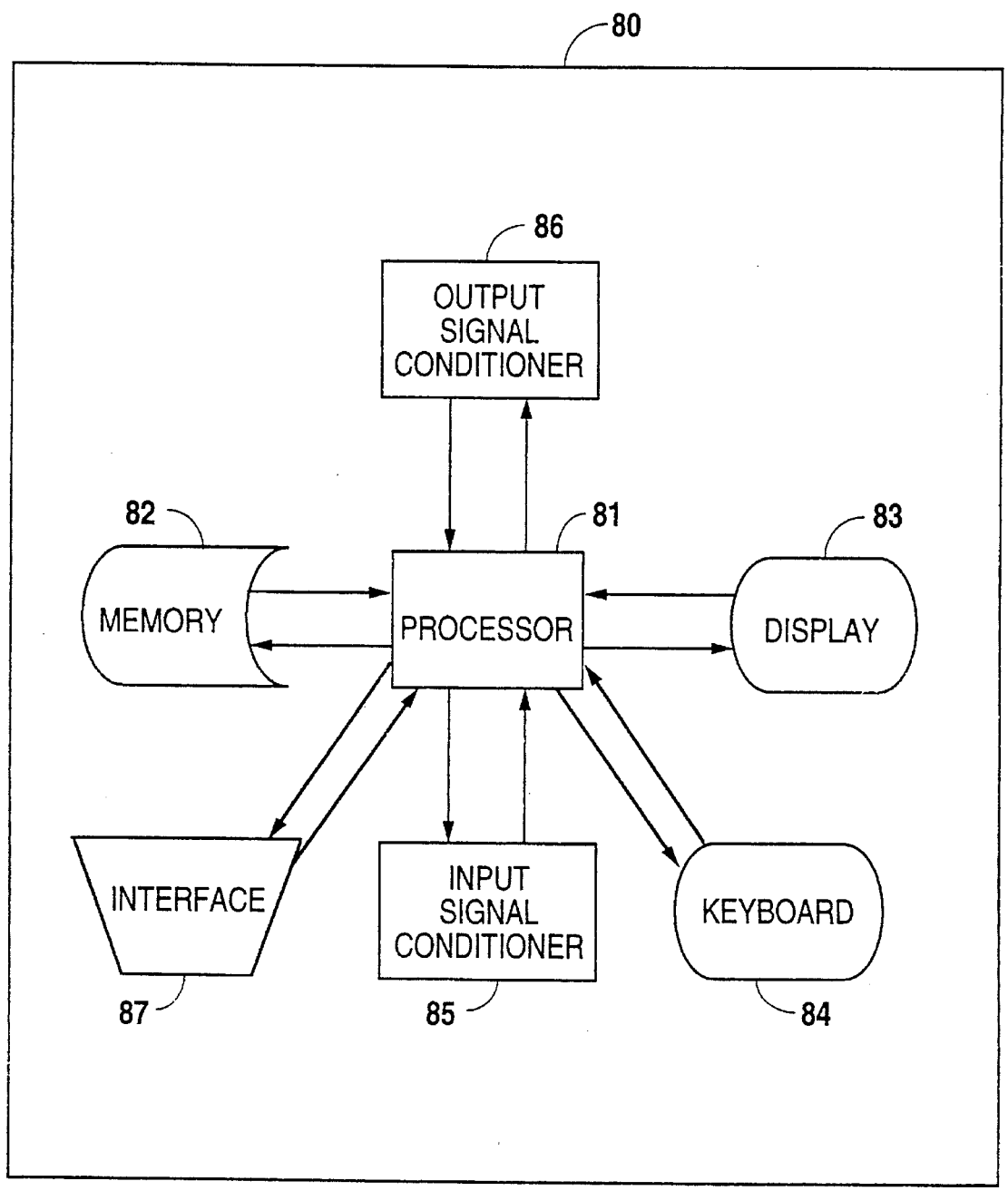
FIG. 2 schematically illustrates an analyzer controller for the analyzer of FIG. 1.

The analyzer has at least one pressure sensor 36 for producing a signal indicative of pressure within cylinder 95, at least one temperature sensor 38 for producing a signal indicative of temperature within cylinder 95, and at least one temperature sensor 47 for producing a signal indicative of fluid temperature of fluid within the fluid inlet pipe An analyzer controller 80, operating through output signal conditioner 86 (see FIG. 2), produces (set point) control signals for the cylinder temperature control means 70, the adjustable piston rod driver 96, and the inlet valves 40,41,42 and outlet valve 60. The control signals are functions of (input) signals passing through input signal conditioner 85 from first and second piston position sensors 28,29 respectively, from cylinder pressure sensor 36, from cylinder temperature sensor 38, and from at least one fluid inlet fluid temperature sensor 47.

The analyzer controller 80 comprises calculator means for calculating a volume correction as a function of the fluid temperature of fluid within the fluid inlet pipe 33, for calculating a vapor pressure value for a liquid within cylinder 95, for calibrating the vapor pressure value against a standard such as hexane or neohexane (which may be conveniently stored in pressurized flasks 43,44 respectively), for calculating a ratio test temperature for a liquid within the cylinder 95, and for calibrating the ratio test temperature against a standard. In the present invention, all calculations related to a volume correction, a vapor pressure value, and a ratio test temperature are carried out using principles of physical chemistry well known to those skilled in the art. Calculations related to calibrations in the present invention all involve comparisons of a new value with an old or standard value, with a decision as to whether to set an alarm if the differences noted in the values exceed a predetermined limit which may be entered into memory 82 (see FIG. 2) of analyzer controller 80 via keyboard 84 and processor 81. Display means for displaying at least the vapor pressure and the ratio test temperature for the liquid within cylinder 95, for the embodiment illustrated in FIG. 1, comprise computer display 83.

Optionally, the above vapor pressure analyzer may additionally comprise an air saturation sensor 46 for producing a signal indicative of air saturation of a fluid within fluid inlet pipe 33. When air saturation sensor 46 is present, analyzer controller 80 additionally comprises calculator means for calculating a vapor pressure correction value as a function of the air saturation of fluid within fluid inlet pipe 33, and calculator means for calculating a ratio test temperature correction value as a function of the air saturation of fluid within fluid inlet pipe 33. Air saturation sensor 46 preferably comprises an electrode for producing a signal indicative of free oxygen in contact with the electrode. From this signal, the partial pressure of oxygen in fluid within fluid inlet pipe 33 may be determined through application of a scale factor furnished with the electrode from the manufacturer. The partial pressure of oxygen may then be used, as a first approximation, to calculate the partial pressure of nitrogen in substantially the same relationship with the partial pressure of oxygen as is found in the ratio of nitrogen to oxygen in air.

The invention also comprises methods for modifying the method of calculating vapor pressure of a liquid test sample according to ASTM D4953 and the method of calculating a ratio test temperature of a liquid test sample according to ASTM D2533, the methods of modification comprising replacement of the test sample volume injection step in each ASTM standard with the following steps: first, measure a temperature of the liquid test sample; second, calculate a volume correction comprising a difference between a standard test sample volume of the liquid at a temperature of 32 degrees Fahrenheit and a standard test sample volume of the liquid at the liquid test sample temperature, the volume correction to be added to the standard test sample volume to form a corrected test sample volume at the liquid test sample temperature; and third, inject the corrected test sample volume of said liquid. These modifications have the effect of ensuring that a predetermined constant mass of test sample liquid is injected with each test.

The invention also comprises methods of modifying the methods of calculating vapor pressure or a ratio test temperature of a liquid test sample according to ASTM D4953 or D2533 respectively. The method of modification comprises replacement of the test sample air saturation step with the following steps: first, measure a temperature of the liquid test sample; second, measure an oxygen tension of the liquid test sample; third, calculate an actual air saturation value leased on the test sample temperature and the test sample oxygen tension; fourth, calculate a vapor pressure correction value or a ratio test temperature correction value based on the actual air saturation value, the vapor pressure correction value or the ratio test temperature correction value to be added to a vapor pressure value or to a ratio test temperature value respectively, as determined for the liquid test sample; and fifth, add the vapor pressure correction value to the determined vapor pressure value to form a corrected vapor pressure value, or add the ratio test correction value to the determined ratio test temperature value to form a corrected ratio test temperature value. Use of these modified methods eliminates the potential for error in the original methods due to failure to adequately air-saturate liquid samples.

In general terms, a vapor pressure analyzer according to the invention may comprise means to measure a temperature of a liquid test sample and means to calculate a liquid test sample volume containing a desired mass of the liquid at the liquid test sample temperature. These temperature measurement means and the following calculation (either by computer or manually) based on physical chemistry principles assure that the appropriate mass of liquid is tested, avoiding the errors which may ensue when a volume measure of fluid is used instead of a mass measure.

The above vapor pressure analyzer further comprises a closed container having adjustable volume (as a piston-cylinder assembly or a bellows), and means to inject the calculated liquid test sample volume into the closed container (as from pressurized liquid containers 43,44,45). The closed container has a first adjusted volume substantially equal to the calculated liquid test sample volume, and means to adjust the closed container volume (with a motor, for example) to a second adjusted volume greater than the first adjusted volume. This expansion step is used in both RPV and ratio test temperature determinations, although the ratio of second adjusted volume to first adjusted volume is about 5:1 for the RPV test and about 21:1 for the ratio test temperature determination. During these volume expansions, temperature control means (conventional closed loop proportional controllers, for example) for maintaining the closed container at a desired temperature are active. Finally, means to measure pressure within said closed container (diaphragm pressure gauges, for example) are employed to gather data on the test outcome.

The above vapor pressure analyzer may additionally comprise means to measure oxygen tension (a commercial process stream oxygen electrode, for example) in the liquid test sample. One would then use means to estimate actual air saturation of the liquid test sample based on the measured liquid test sample oxygen tension which rely on conventional physical chemistry calculations well known to those skilled in the art. Finally, means based on conventional physical chemistry calculations are employed to estimate a corrected pressure within the closed container as a function of the measured pressure within the closed container, the estimated actual air saturation of the liquid test sample, and a desired air saturation of liquid test sample. This correction assures comparability between the corrected pressure and data obtained using conventional techniques where correction factors are not used.

Analyzer tests

The analyzer 99 provides an improved apparatus for determining vapor pressure of volatile crude oil and non-viscous petroleum products other than liquified petroleum gas, as well as the temperature corresponding to a predetermined vapor-liquid ratio (preferably 20:1) at a predetermined pressure (usually 760 mm Hg). The following description relates to one manner of using the analyzer 99, but other procedures are possible.

The analyzer 99 uses the evacuated chamber principle for determining the vapor pressure of a liquid. The method involves heating an initial measured volume of liquid to a first reference temperature, expanding the measured volume substantially greater than the initial measured volume of the liquid, bringing the expanded sample to vapor-liquid equilibrium at a second reference temperature that can, but need not be, the same as the first reference temperature, and measuring the pressure in the initially evacuated zone. Conveniently, both the first and second reference temperatures are 100° F. It is also convenient to have the volume of the evacuated zone at least four times the volume of the initial measure volume of the liquid sample. Specifically, for RVP determination, the evacuated chamber must have a volume five times that of the measured liquid sample.

The stepper-driven piston 10 in cylinder 95 may be temperature controlled using Peltier effect thermal elements or immersed in a circulation temperature bath, either of which control temperature to 100° F±0.2 degrees Fahrenheit. The analyzer 99 then begins by moving the piston 10 between the two optoelectronic sensors 28,29. When this movement is completed, the previous number of stepper motor counts for piston travel between sensors 28 and 29 is compared to the current number, and if a significant difference is noted, an alarm may be displayed on display 83 and the analyzer 99 may cease operation until a reset is performed.

After one or more flushes with the test liquid, the stepper speed may be reduced to increase accuracy in pulling the actual test sample, which may be chilled to 32 F. or which may be at a different temperature. The stepper motor 16 then adjusts the test piston to the user defined (corrected) sample volume as the sample enters the cylinder. After closure of inlet valves 40,41,42 and outlet valve 60, stepper motor 16 then adjusts the piston 10 to the final volume for the selected vapor-to-liquid ratio (4:1 for RVP).

Next the vapor/liquid equilibration procedure begins. It consists of the stepper motor 16 and piston 10 remaining in a static state, with current cylinder temperature and pressure being displayed real-time on the display 83. A predetermined equilibration time is counted down on the display, and when the time is up, (if the cylinder temperature is within predetermined temperature limits) the analyzer controller 80 stores in memory 82 the current cylinder transducer reading as the RVP, and provides the user output to interface 87 (and thence, for example, to a printer). If RVP alarm limits are exceeded, an external relay is tripped, an alarm message transmitted to the printer, and a message generated on the display 83.

When the system is placed in the "on-line" mode by the operator, a software scheduler program stored in memory 82 begins running. It counts down a user defined interval between runs, and when the time is up, begins sampling the next sample source in the sequence enabled by the operator. The sample source can come from the "unknown sample" stream (for example, pressurized flask 45), or from the "standard sample" rack (for example, pressurized flasks 43,44). The number of sample runs between standard runs is user defined, and the user may associate an unknown stream with a particular standard source. The number of RVP runs between a scheduled ratio test temperature determination is also set up by the user.

What is claimed is:

1. A vapor pressure analyzer, comprising
    a hollow cylinder of substantially right circular cylindrical shape, said cylinder having a wall, first and second ends and a longitudinal axis passing through and substantially parallel to said first and second ends;
    cylinder temperature control means for attaining a desired temperature within said cylinder;
    a piston positionable slidingly and sealingly within said hollow cylinder;
    a piston rod coupled to said piston and passing slidingly and sealingly through a hole in said first cylinder end to control longitudinal movement of said piston within said cylinder;
    an adjustable piston rod driver coupled to said piston rod for adjusting piston longitudinal position within said cylinder and for producing a signal indicative of said piston longitudinal position within said cylinder;
    calibration means for calibrating said adjustable piston rod driver by reference to at least one prior adjustable piston rod calibration;
    first and second piston position sensors within said cylinder wall proximate said first and second cylinder ends respectively for producing first and second piston position sensor signals indicative of first and second longitudinal piston positions within said cylinder;
    an inlet port and an outlet port in said cylinder first end;
    a fluid inlet pipe and a fluid outlet pipe coupled sealingly to said inlet and outlet ports respectively;
    at least one inlet valve and an outlet valve in line with said fluid inlet and outlet pipes respectively; and
    at least one pressure sensor for producing a signal indicative of pressure within said cylinder;
    at least one temperature sensor for producing a signal indicative of cylinder temperature;
    at least one temperature sensor for producing a signal indicative of fluid temperature of fluid within said fluid inlet pipe;
    an analyzer controller to produce control signals for said cylinder temperature control means, said adjustable piston rod driver, and said inlet and outlet valves as functions of first and second piston position sensor signals, a cylinder pressure signal, at least one cylinder temperature signal, and at least one fluid inlet fluid temperature signal, said analyzer controller comprising
        calculator means for calculating a volume correction as a function of said fluid temperature of fluid within said fluid inlet pipe;
        calculator means for calculating a vapor pressure value for a liquid within said cylinder;
        calibration means for calibrating said vapor pressure value against a standard;
        calculator means for calculating a ratio test temperature for a liquid within said cylinder;
        calibration means for calibrating said ratio test temperature against a standard;
        display means for displaying at least said vapor pressure and said ratio test temperature for said liquid within said cylinder.

2. The vapor pressure analyzer of claim 1, additionally comprising
    an air saturation sensor for producing a signal indicative of air saturation of a fluid within said fluid inlet pipe;
    calculator means for calculating a vapor pressure correction value as a function of said air saturation of fluid within said fluid inlet pipe; and
    calculator means for calculating a ratio test temperature correction value as a function of said air saturation of fluid within said fluid inlet pipe.

3. The vapor pressure analyzer of claim 2 wherein said air saturation sensor comprises an electrode for producing a signal indicative of free oxygen in contact with said electrode.

4. The vapor pressure analyzer of claim 1 wherein said first and second piston position sensors are optoelectronic.

5. The vapor pressure analyzer of claim 1 wherein said cylinder temperature control means comprises at least one Peltier effect thermal element thermally coupled to said cylinder.

6. The vapor pressure analyzer of claim 5 wherein said cylinder temperature control means further comprises at least one Peltier effect thermal element thermally coupled to said piston.

7. The vapor pressure analyzer of claim 1 wherein said adjustable piston rod driver comprises a stepper motor driven lead screw.

8. The vapor pressure analyzer of claim 7 wherein said analyzer controller comprises an electronic computer having a stored program.

9. The vapor pressure analyzer of claim 8 further comprising storage means for storing at least said signal indicative of said piston longitudinal position within said cylinder.

10. The vapor pressure analyzer of claim 9 further comprising storage means for storing at least said vapor pressure and said ratio test temperature values for a liquid within said cylinder.

11. The vapor pressure analyzer of claim 10 further comprising a stored program for calibration of said adjustable piston rod driver, said stored calibration program comprising the steps storing a standard value of stepper motor pulses to move said piston from a first position proximate said first piston position sensor to a second position proximate said second piston position sensor;

commanding said adjustable piston rod driver to move said piston to said first position proximate said first piston position sensor;

commanding said adjustable piston rod driver to move said piston to said second position proximate said second piston position sensor;

counting stepper motor pulses required to move said piston from said first position to said second position to form a new sum of stepper motor pulses;

subtracting said standard value of stepper motor pulses from said new sum of stepper motor pulses to form a pulse error value; and setting an alarm if said pulse error value exceeds a previously determined pulse error limit.

* * * * *